US00PP31938P2

(12) United States Plant Patent
van Geest

(10) Patent No.: US PP31,938 P2
(45) Date of Patent: Jul. 7, 2020

(54) ***FICUS* PLANT NAMED 'ESPE1703'**

(50) Latin Name: *Ficus benjamina*
Varietal Denomination: ESPE1703

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,276

(22) Filed: Mar. 16, 2019

(51) Int. Cl.
*A01H 5/12* (2018.01)

(52) U.S. Cl.
USPC ..... Plt./211

(58) Field of Classification Search
USPC ..... Plt./211
CPC ..... A01H 5/12
See application file for complete search history.

(56) References Cited

PUBLICATIONS

PLUTO Plant Variety Database Nov. 6, 2019.*

* cited by examiner

*Primary Examiner* — Annette H Para
(74) *Attorney, Agent, or Firm* — Samuel R. McCoy, Jr.

(57) ABSTRACT

A new and distinct variety of *Ficus* plant named 'ESPE1703' which is characterized by the combination of a compact growth habit, large foliage relative to the small stems, dark green foliage that is blotched yellow-green and irregularly and broadly margined yellow to green-white, and the stability of all characteristics from generation to generation.

2 Drawing Sheets

Latin name of the genus and species: The Latin name of the genus and species of the novel variety disclosed herein is *Ficus benjamina.*

Variety denomination: The inventive variety of *Ficus* disclosed herein has been given the variety denomination 'ESPE1703'.

BACKGROUND OF THE INVENTION

Parentage: 'ESPE1703' originated as a naturally occurring, whole-plant mutation of *Ficus benjamina* 'Twilight'. In the summer of 2016, the inventor discovered the mutation at his commercial greenhouse in Gravenzande, The Netherlands, growing amongst a cultivated population of 'Danielle' plants. The mutation was noted for its compact habit and variegated foliage and was subsequently isolated for further evaluation in order to confirm the distinctness and stability of the characteristics first observed. Upon confirmation of distinctness and stability, 'ESPE1703' was selected for commercialization.

Asexual Reproduction: Asexual reproduction of 'ESPE1703', by way of stem cuttings, was first initiated in the summer of 2016 at a commercial greenhouse in Gravenzande, The Netherlands. Through five subsequent generations, the unique features of this cultivar have proven to be stable and true to type.

SUMMARY OF THE INVENTION

The cultivar 'ESPE1703' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE1703'. These characteristics in combination distinguish 'ESPE1703' as a new and distinct *Ficus* cultivar:

1. *Ficus* 'ESPE1703' exhibits a compact growth habit; and
2. *Ficus* 'ESPE1703' exhibits large foliage relative to the small stems; and
3. *Ficus* 'ESPE1703' exhibits dark green foliage that is blotched yellow-green and irregularly and broadly margined yellow to green-white.

BOTANICAL DESCRIPTION OF THE PLANT

Figure 1:
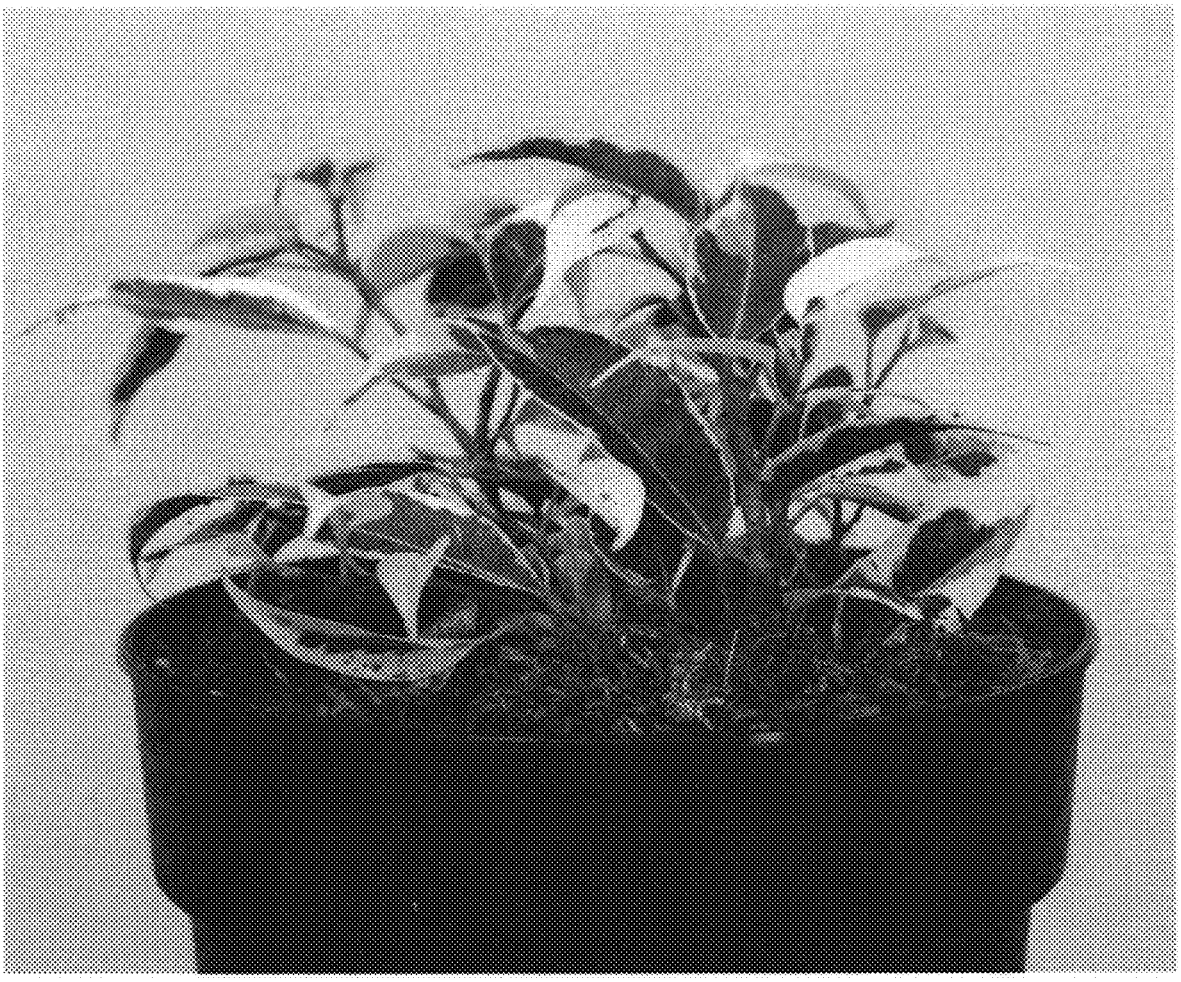
FIG. 1 illustrates, as nearly true as it is reasonably possible to make the same in color photographs of this type, an exemplary plant of 'ESPE1703' grown in a commercial greenhouse in Gravenzande, The Netherlands. This plant is approximately 26 weeks old, shown planted in a 15 cm container.
Figure 2:
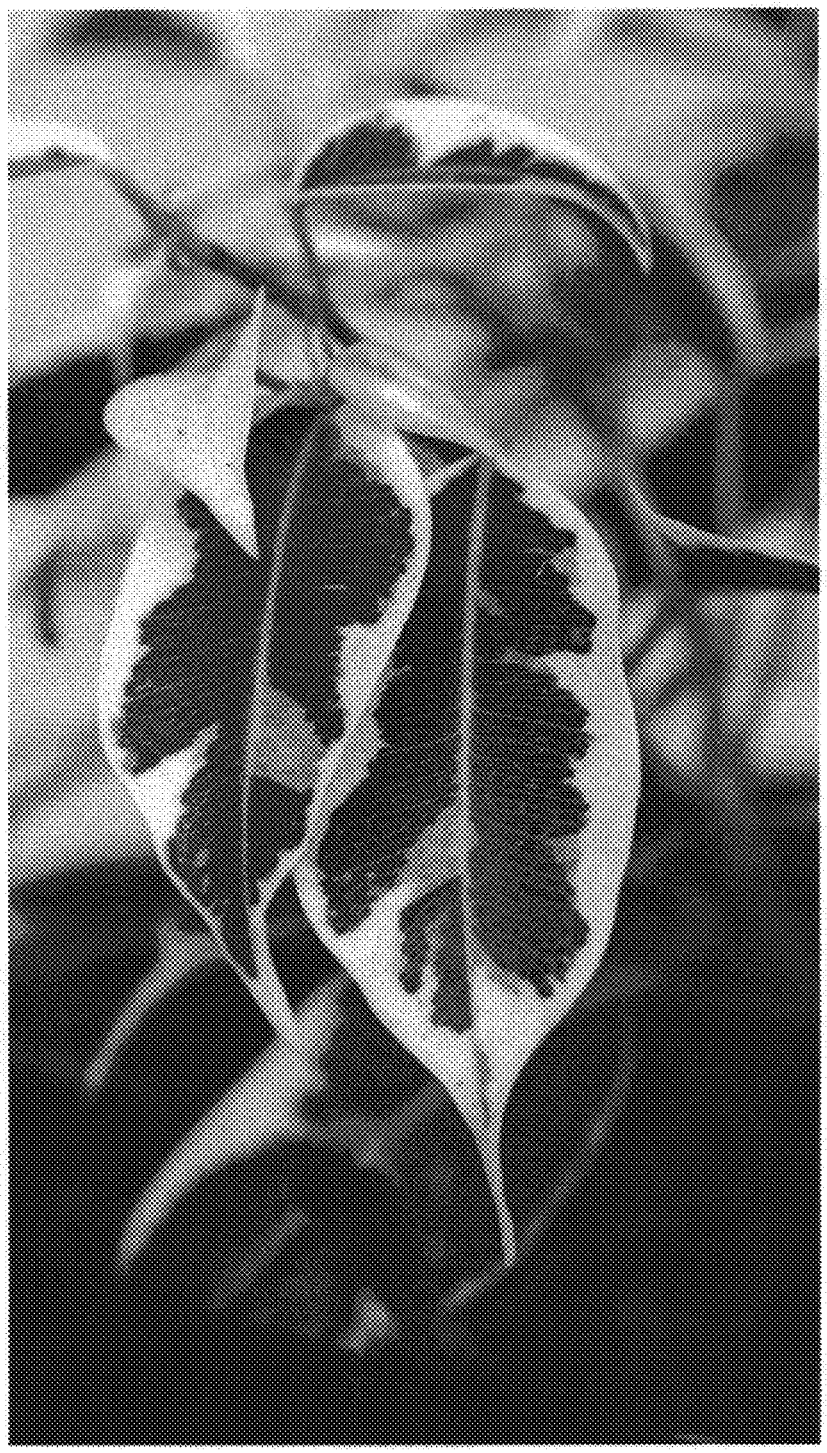
FIG. 2 illustrates, as nearly true as it is reasonably possible to make the same in color photographs of this type, the typical foliage of 'ESPE1703'.

The following observations and measurements were made in February of 2019 and describe a sample set of six 26 week-old 'ESPE1703' plants grown in 10.5 cm nursery pots, two plants per container, at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE1703' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'ESPE1703' and comparisons with the parent plant and most similar commercial variety of *Ficus* are provided below.

Plant description:

*Growth habit*.—Broad, upright perennial.

*Plant form*.—Orbicular to ovate.

*Average height*.—7.3 cm from the soil level to the top of the foliar plane.

*Plant spread*.—Average of 10.3 cm.

*Growth rate*.—Slow.

*Plant vigor*.—Low to moderately vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 16 weeks to produce a marketable finished plant in a 14 cm pot.

*Disease resistance*.—Neither resistance nor susceptibility to typical *Ficus benjamina* pests and diseases has been observed.

*Environmental tolerances*.—Adapt to, at least, USDA Zones 10 through 13 and temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Moderately deep.

*Diameter of roots*.—0.5 mm on average.

*Texture*.—Smooth; no root hairs.

*Color*.—Greyed-yellow, nearest to RHS 162B.

Stem:

*General branching habit*.—Basally branching main stems; with lateral branching. Pinching isn't required but will improve branching. Stems produce a milky exudate when damaged.

*Main stem*.—Quantity — 2. Attitude — Upright. Aspect — Rounded. Strength — Strong. Color, immature stems — Yellow-green, nearest to RHS 145B. Color, mature stems — Yellow-green, nearest to RHS 152B. Color at internodes — Yellow-green, nearest to RHS 152B. Color, oldest wood — Greyed-brown, nearest to RHS 199B. Texture — Densely covered with a fibrous layer, colored greyed-brown, nearest to a mixture of RHS 199C and 199D. Luster — Matte.

*Lateral branches*.—Quantity — 5. Length — 3.7 cm. Diameter — 1.0 cm. Internode length — 0.7 cm. Attitude — Outward; at an approximate angle of 40 degrees to the main stems. Aspect — Rounded. Strength — Strong. Texture — Densely covered with a fibrous layer, colored greyed-brown, nearest to a mixture of RHS 199C and 199D. Luster — Matte. Color, immature stems — Yellow-green, nearest to RHS 145B. Color, mature stems — Yellow-green, nearest to RHS 152B. Color at internodes — Yellow-green, nearest to RHS 152B.

Foliage:

*Arrangement*.—Alternate.

*Division*.—Simple.

*Quantity*.—6 leaves per lateral branch.

*Attitude*.—At an average angle of 45 degrees to the branch.

*Lamina*.—Shape — Narrowly ovate to oblong. Aspect — Slightly carinate. Dimensions — 3.8 cm long and 1.5 cm wide. Apex — Apiculate to aristate. Base — Acuminate. Margin — Entire to slightly sinuate; slightly repand. Texture and luster of the adaxial surface — Smooth, glabrous, and matte. Texture and luster of the abaxial surface — Smooth, glabrous, and matte. Color — Juvenile foliage, adaxial surface — Yellow-green, nearest to RHS 144B, and blotched lighter, nearest to a combination of RHS 145C and 145D; irregularly and broadly margined green-white, nearest to RHS 157C. Juvenile foliage, abaxial surface — Yellow-green, nearest to RHS 146D, and blotched lighter, nearest to RHS 145C; irregularly and broadly margined green-white, nearest to RHS 157C. Mature foliage, adaxial surface — Green, nearest to RHS NN137A, and blotched yellow-green, nearest to RHS 148D; irregularly and broadly margined yellow to green-white, nearest to a mixture of RHS 4D and 157C. Mature foliage, abaxial surface — Green, nearest to RHS NN137D, and blotched greyed-green, nearest to RHS 191B; irregularly and broadly margined yellow, nearest to a mixture of RHS 4D. Venation — Pattern — Pinnate. Color, adaxial surface — Green, nearest to RHS 138C. Color, abaxial surface — Green, nearest to RHS 138D.

*Stipule*.—Not present.

*Petiole*.—Length — 1.0 cm. Diameter — 0.8 cm. Strength — Moderately strong. Texture — Smooth; glabrous. Luster — Very slightly glossy. Color, adaxial surface — Yellow-green, nearest to a combination of RHS 144B and 144C. Color, abaxial surface — Yellow-green, nearest to a combination of RHS 144B and 144C.

Inflorescence: No flowering has been observed to date.

COMPARISON WITH THE PARENT PLANT

Plants of the new cultivar 'ESPE1703' differ from the parent, *Ficus benjamina* 'Twilight' (not patented) in the following characteristics described in Table 1 below.

TABLE 1

| Characteristic | 'ESPE1703' | 'Twilight' |
|---|---|---|
| Plant size. | Smaller than 'Twilight'. | Larger than 'ESPE1703'. |
| General coloration of the foliage. | Darker green and more narrowly margined yellow to green-white. | Lighter green and more broadly margined yellow to green-white. |
| Prominence of foliage venation. | Veins are less prominent. | Veins are more prominent. |

COMPARISON WITH THE CLOSEST KNOWN COMPARATOR

Plants of the new cultivar 'ESPE1703' differs from the variety, *Ficus benjamina* 'ESPE1702', for which a United States plant patent application is being filed concurrently with the instant application, in the following characteristics described in Table 2 below.

TABLE 2

| Characteristic | 'ESPE1703' | 'ESPE1702' |
|---|---|---|
| General plant profile. | Shorter and wider than 'ESPE1702'. | Slightly taller and narrower than 'ESPE1703'. |

TABLE 2-continued

| Characteristic | 'ESPE1703' | 'ESPE1702' |
|---|---|---|
| Abundance of foliage. | More abundant. | Less abundant. |
| Foliage attitude. | More relaxed. | More upright. |
| General coloration of the foliage. | Green and blotched yellow-green; irregularly and broadly margined yellow to green-white. | Green. |

That which is claimed is:

1. A new and distinct variety of *Ficus* plant named 'ESPE1703', substantially as described and illustrated herein.

* * * * *